(12) United States Patent
Siddiqui et al.

(10) Patent No.: US 6,215,317 B1
(45) Date of Patent: Apr. 10, 2001

(54) METHOD AND APPARATUS FOR MEASURING IN-PLACE DENSITY AND MOISTURE CONTENT

(75) Inventors: Shafiqul I. Siddiqui, Mishawaka; Vincent P. Drnevich, West Lafayette, both of IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/300,208

(22) Filed: Apr. 27, 1999

(51) Int. Cl.$^7$ .................... G01R 27/04; G01R 27/28
(52) U.S. Cl. .................... 324/643; 324/637; 324/690
(58) Field of Search .................... 324/642, 643, 324/690, 637

(56) References Cited

U.S. PATENT DOCUMENTS

| | | | |
|---|---|---|---|
| 4,154,552 | 5/1979 | Van Bilderbeek | 405/229 |
| 4,219,776 | 8/1980 | Arulanandan | 324/323 |
| 4,352,059 | 9/1982 | Suh et al. | 324/61 |
| 4,808,185 | 2/1989 | Penenberg et al. | 623/20 |
| 4,848,422 | 7/1989 | Chiantella | 142/37 |
| 4,929,885 | 5/1990 | Dishman | 324/664 |
| 5,136,249 | 8/1992 | White et al. | 324/643 |
| 5,424,649 | 6/1995 | Gluck | 324/643 |
| 5,459,403 | 10/1995 | Kohler | 324/643 |
| 5,479,104 | 12/1995 | Cambell | 324/690 |
| 5,663,649 | 9/1997 | Topp | 324/643 |
| 5,801,537 | * 9/1998 | Siddiqui et al. | 324/643 |
| 5,804,976 | 8/1998 | Gaskin | 324/643 |
| 5,933,015 | * 8/1999 | Siddiqui et al. | 324/643 |

OTHER PUBLICATIONS

Topp, G.C.; "Electromagnetic Determination of Soil Water Contents: Measurements in Coaxial Transmission Lines"; Water Resources Research, vol. 16, No. 3, Jun. 1980, pp. 574–582.

Zegelin, S.J.; "Improved Field Probes for Soil Water Content and Electrical Conductivity Measurement Using Time Domain Reflectometry"; Water Resources Research; vol. 25, No. 11, Nov. 1989. pp. 2367–2376.

Baran, Ed; "Use of Time Domain Reflectometry for Monitoring Moisture Changes in Crushed Rock Payments," pp. 349–356, United States Bureau of Mines Symposium and Workshop on Time Domain Reflectometry in Environmental, Infrastructure, and Mining Applications, Sep. 7, 1994.

Kotdawala, Shrinath J.; "Use of Time Domain Reflectometry for Monitoring Moisture Changes in Crushed Rock Payments," pp. 364–373, United States Bureau of Mines Symposium and Workshop on Time Domain Reflectometry in Environmental, Infrastructure, and Mining Applications, Sep. 7, 1994.

Rada, Gonzalo R.; "Use of Time Domain Reflectometry for Monitoring Moisture Changes in Crushed Rock Payments," pp. 422–433, United States Bureau of Mines Symposium and Workshop on Time Domain Reflectometry in Environmental, Infrastructure, and Mining Applications, Sep. 7, 1994.

* cited by examiner

Primary Examiner—Safet Metjahic
Assistant Examiner—J. Kerveros
(74) Attorney, Agent, or Firm—Woodard, Emhardt, Naughton, Moriarty & McNett

(57) ABSTRACT

A method and apparatus for measuring in-place soil density and moisture content. A cylindrical cell is disclosed which may be used to measure the density and the dielectric constant of a soil sample placed within the cylindrical cell. Also disclosed is a multiple rod probe which is designed to contact spikes driven into the ground to measure the in-place dielectric constant of soil. The multiple rod probe includes adjustable studs which ensure complete contact with the spikes. Both measurements are performed using time domain reflectometry. The present invention develops equations for determining the density of the soil in-place from the measured dielectric constant of the soil in-place and the measured density and dielectric constant of the soil in the cylindrical cell.

3 Claims, 9 Drawing Sheets

METHOD AND APPARATUS FOR MEASURING IN-PLACE DENSITY AND MOISTURE CONTENT

This invention was made with Government support from the Indiana Department of Transportation/Federal Highway Administration. The Government has certain rights in the invention.

TECHNICAL FIELD OF THE INVENTION

The present invention generally relates to scientific measurement methods and apparatus and, more particularly, to a method and apparatus for measuring in-place soil density and moisture content.

BACKGROUND OF THE INVENTION

For the past 20 years, time domain reflectometry has been used to measure the volumetric moisture content of soils (volume of moisture per unit volume of soil), mostly in the field of soil science. As shown in FIG. 1, these measurements involved the insertion of a probe 10 comprising a central rod 12 and two or more peripheral rods 14 into the soil 16 to be measured. The peripheral rods 14 (which are preferably three in number) are spaced equidistant from the central rod 12 and equidistant from each other. A coaxial transmission line 18 is then coupled to the structure with the center conductor of the coaxial cable 18 coupled to the center rod 12 and the exterior shield (outer conductor) of the coaxial cable 18 coupled to each of the peripheral rods 14. In this way, the peripheral rods 14 simulate the effects of a continuous outer coaxial shield in the soil 16, without the requirement of attempting to drive a cylindrical probe into the soil 16. Time domain reflectometry analysis equipment 20 is then coupled to the coaxial cable 18, and the reflections of high frequency electrical signals from the soil 16 are measured using the analysis equipment 20. These reflections will change in predictable ways depending upon the dielectric constant of the soil 16, which has been found to be strongly correlated with the volumetric moisture content of the soil 16. Therefore, time domain reflectometry has been established as a viable tool for measuring volumetric moisture content of a soil.

The prior art probes such as those illustrated in FIG. 1 are intended for permanent installation at a measurement location with periodic measurements being made through the probe 10 over a period of time. Physically, the prior art probes 10 are not rugged enough to withstand repeated insertion into and extraction from hard soils. The prior art robes 10 are not suitable as portable probes to be used for rapid insertion and removal following one-time soil measurement at a variety of locations within a soil field to be measured. There is therefore a need for a probe design which is rugged enough to withstand repeated insertions and extractions from dense soil, thereby facilitating the taking of one-time measurements at multiple locations. The present invention is directed toward meeting this need.

Although time domain reflectometry techniques are useful in measuring volumetric moisture content of soils, they cannot be presently used to measure gravimetric moisture content of soils (weight of moisture per unit weight of soil solids). Many applications in geotechnical engineering require a knowledge of the gravimetric moisture content of soil. In order to convert from the volumetric moisture content measured by time domain reflectometry to the gravimetric moisture content, it is necessary to know the density of the soil. There are several prior art methods for measuring in-place density in moisture content of soils, such as the sand-cone method, the rubber balloon method and the drive tube method. These methods are difficult and time consuming and are usually accompanied by the oven drying method of measuring moisture content in order to measure in-place dry density and moisture content of the soil. The oven drying method of measuring moisture content requires a significant waiting time before measurement results are available. Another method, the nuclear method of measuring in-place soil moisture content and density requires extensive calibration. Moreover, the nuclear method is potentially hazardous because it utilizes radioactive materials. There is therefore a need for a technique to measure in-place gravimetric moisture content and density quickly, precisely, and preferably in a non-destructive manner. The present invention is directed toward meeting this need.

SUMMARY OF THE INVENTION

The present invention relates to a method and apparatus for measuring in-place soil density and moisture content. A cylindrical cell is disclosed which may be used to measure the density and the dielectric constant of a soil sample placed within the cylindrical cell. Also disclosed is a multiple rod probe which is designed to contact spikes driven into the ground to measure the in-place dielectric constant of soil. The multiple rod probe includes adjustable studs which ensure complete contact with the spikes. Both measurements are performed using time domain reflectometry. The present invention develops equations for determining the density of the soil in-place from the measured dielectric constant of the soil in-place and the measured density and dielectric constant of the soil in the cylindrical cell.

In one form of the invention an apparatus for measuring a moisture content of a soil sample is disclosed, comprising a container having a closed first end, an open second end and a substantially cylindrical conductive sidewall defining an interior volume adapted to receive the soil sample; a template having a central opening therethrough that is coaxial with a longitudinal axis of the sidewall, the template adapted to be removable mounted to the open second end; a hand penetrometer having an elongated rod sized to be inserted through the template central opening and into the soil sample such that a hollow shaft is created along the longitudinal axis; and a cap adapted to be removably mounted to the open second end after the hollow shaft has been created and after the template has been removed from the open second end, the cap comprising: a conductive head adapted to contact the sidewall; a conductive central rod; and a first annular non-conductive spacer coupling the conductive head to the conductive central rod; wherein the central rod substantially fills the hollow shaft when the cap is mounted to the open second end; wherein the assembled container, soil sample and cap form a coaxial transmission line wherein the soil sample serves as a dielectric.

In another form of the invention a method of preparing a soil sample for measurement of a moisture content of the soil sample is disclosed, comprising the steps of: (a) providing a container having a closed first end, an open second end and a substantially cylindrical conductive sidewall defining an interior volume adapted to receive the soil sample; (b) removably mounting a template to the open second end, wherein the template has a central opening therethrough that is coaxial with a longitudinal axis of the sidewall; (c) inserting an elongated rod through the template central opening and into the soil sample such that a hollow shaft is created along the longitudinal axis; (d) removing the elongated rod; (e) removing the template; (f) providing a cap, comprising: a conductive head adapted to contact the sidewall; a conductive central rod; and an annular non-conductive spacer coupling the conductive head to the conductive central rod; and (g) mounting the cap to the open second end such that the central rod substantially fills the hollow shaft, wherein the assembled container, soil sample and cap form a coaxial transmission line wherein the soil sample serves as a dielectric.

In another form of the invention an apparatus for measuring moisture content of an in-place soil sample is disclosed, comprising a template having a central hole therethrough and a plurality of peripheral holes therethrough, the plurality of peripheral holes being substantially equidistant from the central hole; a plurality of spikes adapted to be driven through the central and peripheral holes of the template and into the soil sample; and a probe head, comprising: an annular conductive body; a plurality of conductive peripheral studs mounted to a bottom surface of the body; a conductive central stud; and an annular non-conductive insert coupling the body to the central stud; wherein a first spacing between the central stud and the peripheral studs is substantially the same as a second spacing between the central hole and the peripheral holes, such that each stud is aligned with a respective spike when the probe head is placed over the spikes after they have been driven into the soil sample.

In another form of the invention an apparatus for measuring moisture content of an in-place soil sample is disclosed, comprising an annular conductive body; a plurality of conductive peripheral studs adjustably mounted to a bottom surface of the body, such that an extension of each of the peripheral studs away from the body may be adjusted; an annular non-conductive insert coupled to the body; a conductive central stud adjustably mounted to the insert such that an extension of the central stud away from the insert may be adjusted.

In another form of the invention a method of installing an apparatus for measuring a dielectric constant of an in-place soil sample is disclosed, comprising the steps of: (a) providing a template having a central hole therethrough and a plurality of peripheral holes therethrough, the plurality of peripheral holes being substantially equidistant from the central hole; (b) laying the template on a surface of the in-place soil sample; (c) driving a plurality of conductive spikes into the soil through the central hole and each of the peripheral holes of the template; (d) removing the template; (e) providing a probe head, comprising: an annular conductive body; a plurality of conductive peripheral studs mounted to a bottom surface of the body; a conductive central stud; and an annular non-conductive insert coupling the body to the central stud; wherein a first spacing between the central stud and the peripheral studs is substantially the same as a second spacing between the central hole and the peripheral holes, such that each stud is aligned with a respective spike when the probe head is placed over the spikes after they have been driven into the soil sample; (f) placing the probe head onto the conductive spikes, such that each stud is aligned with a respective spike.

In another form of the invention a method of installing an apparatus for measuring a dielectric constant of an in-place soil sample is disclosed, comprising the step of: (a) providing a template having a central hole therethrough and a plurality of peripheral holes therethrough, the plurality of peripheral holes being substantially equidistant from the central hole; (b) laying the template on a surface of the in-place soil sample; (c) driving a plurality of conductive spikes into the soil through the central hole and each of the peripheral holes of the template; and (d) removing the template.

In another form of the invention a method of installing an apparatus for measuring a dielectric constant of an in-place soil sample is disclosed, comprising the steps of: (a) providing a probe head, comprising: an annular conductive body; a plurality of conductive peripheral studs mounted to a bottom surface of the body; a conductive central stud; and an annular non-conductive insert coupling the body to the central stud; wherein the central stud and the peripheral studs are arranged in a first pattern; (b) driving a plurality of conductive spikes into the soil, wherein the spikes are arranged in the first pattern; and (c) placing the probe head onto the conductive spikes, such that each stud is aligned with a respective spike.

In another form of the invention a template for guiding an installation of spikes into an in-place soil sample in a predetermined pattern is disclosed, comprising a plurality of template sections which fit together to form the template, wherein a plurality of holes are formed through the template, each hole straddling an intersection between two or more template sections; at least one hinge coupling the plurality of template sections to one another; and a releasable coupling joining two of the plurality of template sections to one another; wherein the assembled template forms the holes into the predetermined pattern, thereby allowing the spikes to be driven into the soil through the holes; and wherein the releasable coupling may be released after the spikes have been driven into the soil, thereby allowing each template section to be swung away from the spikes by rotating each template section about its attached hinge.

DESCRIPTION OF THE PREFERRED EMBODIMENT

Figure 1:
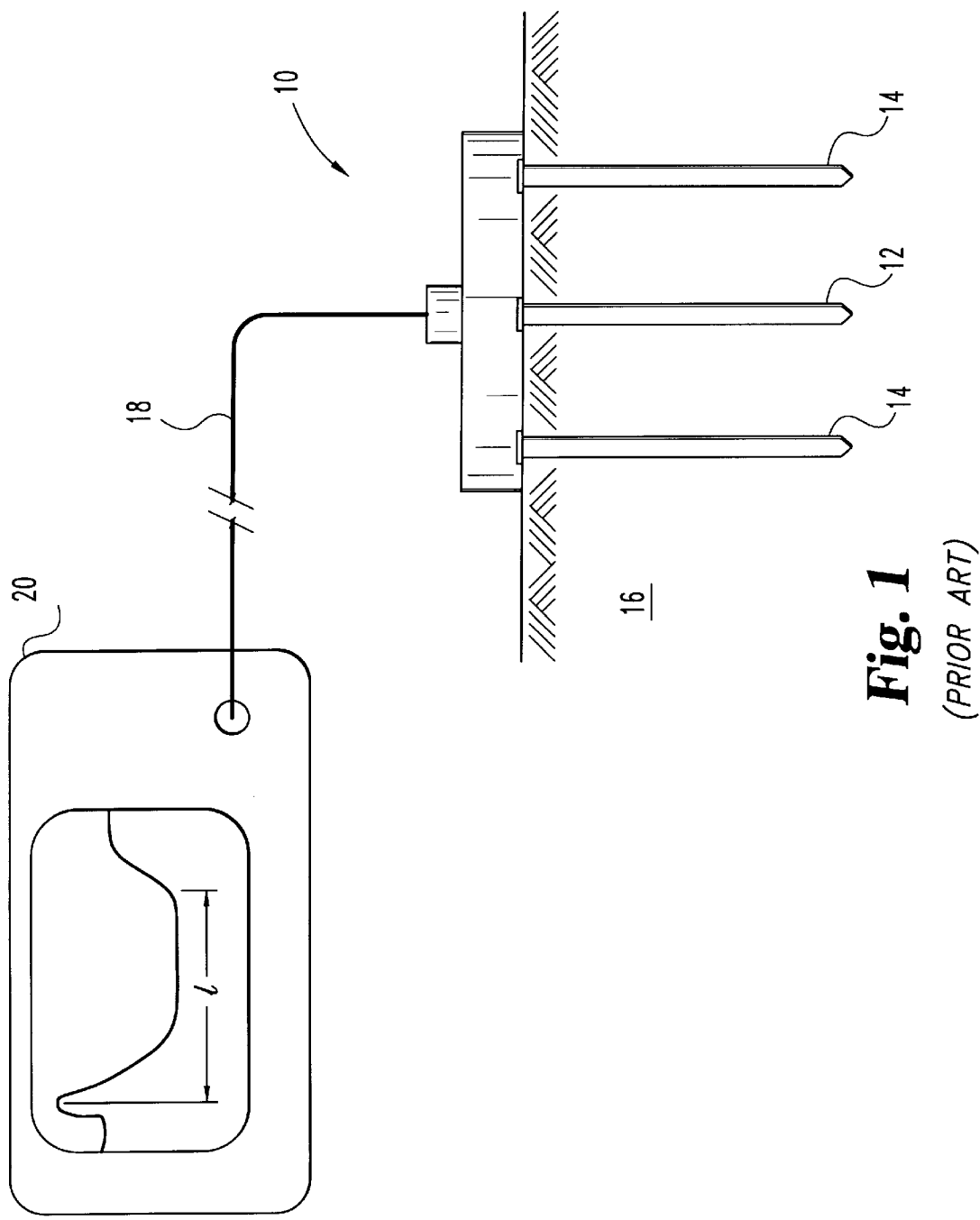
FIG. 1 is a side elevational view of a prior art probe for measuring the dielectric constant of an in-place soil sample.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The time domain reflectometry (TDR) technique measures the velocity of an electromagnetic wave traveling through a transmission line (TL). This velocity (v) is related to the dielectric constant of the insulating medium between the conductors of the transmission line as given by $$v = \frac{c}{K^{0.5}} \quad (1)$$

where c is the velocity of light in a vacuum ad K is the dielectric constant of the medium.

A TDR probe 10 for measuring soil moisture content is actually a transmission line whose dielectric medium is soil when this probe is driven into soil 16. This probe 10 is connected with the TDR instrument 20 via a coaxial cable 18. The TDR device 20 sends a step pulse down the cable 18. When this signal reaches the beginning of the probe 10, a portion of the signal is reflected back to the TDR device 20. When the rest of the signal reaches the end of the probe 10, another reflection of the signal occurs. These two reflections cause two discontinuties in the resulting signal displayed on the TDR device 20 screen. The time difference between these two discontinuties is the time (t) required by the signal to travel twice the length (L) of the probe in soil. So the wave propagation velocity in soil is $$v_s = \frac{2L}{t} \quad (2)$$

and the dielectric constant of soil is (using Eq. 1)

$$K = (ct/2L)^2 \quad (3)$$

In commercial TDR instruments, the term ct/2 is reduced to an apparent length (l) resulting in $$K = \frac{l^2}{L^2} \quad (4)$$

Research over the last 20 years, mostly in soil science, has shown that the dielectric constant of soil is directly related to the volumetric moisture content of soil. Volumetric moisture content (volume of moisture per unit volume of soil) is related with gravimetric moisture content(weight of moisture per unit weight of soil solids) as $$w = \frac{\theta}{\rho_d} \rho_w \quad (5)$$

where: w is the gravimetric moisture content of the soil, $\theta$ is the volumetric moisture content of soil, $\rho_d$ is the dry density of soil and $\rho_w$ is the density of water. In geotechnical engineering, moisture content is usually measured in terms of gravimetric moisture content.

An empirical relationship between the dielectric constant and the volumetric moisture content of soil is $$\theta = -0.053 + 2.92 \times 10^{-2} K - 5.5 \times 10^{-4} K^2 + 4.3 \times 10^{-6} K^3 \quad (6)$$

where $\theta$ is the volumetric moisture content of soil. Equation 6 is not appropriate for organic soils or heavy clays. It has been recommended to use a soil specific calibration equation where Eq. 6 does not provide sufficiently accurate results. Recent studies have developed better relationships to correlate K–$\theta$. It has been observed that there exists a linear relationship between $\theta$ and $K^{0.5}$ (if the density of soil does not vary much) of the form $$K^{0.5} = c_1 + c_2 \theta \quad (7)$$

where $c_1$ and $c_2$ are constants for specific soil type. It has been reported that $c_1$ and $c_2$ also depend on density of soil. Depending on soil type and density, $c_1$ may vary between approximately 1.2 to 1.6 and $c_2$ may vary between approximately 7.8 to 9.7. The present invention uses Eqs. 6 and 7 for measuring moisture content and discloses yet another equation for measuring moisture content hereinbelow.

The existence of a direct correlation between $K^{0.5}$ and $\theta$ as expressed in Eq. 7 is the theoretical basis for measuring in-place density and moisture content. Using Eq. 5, gravimetric moisture content can be calculated from $\theta$ if the density of the soil is known, and density can be calculated from $\theta$ if the gravimetric moisture content is known.

The in-place density of the soil, however, cannot be directly measured. The present invention solves this problem by correlating measurements made on a sample of the soil placed in the cylindrical cell (CC) 30 of FIG. 2A with measurements made in-place with the multiple rod probe (MRP) 70 of FIG. 3.

Figure 2A:
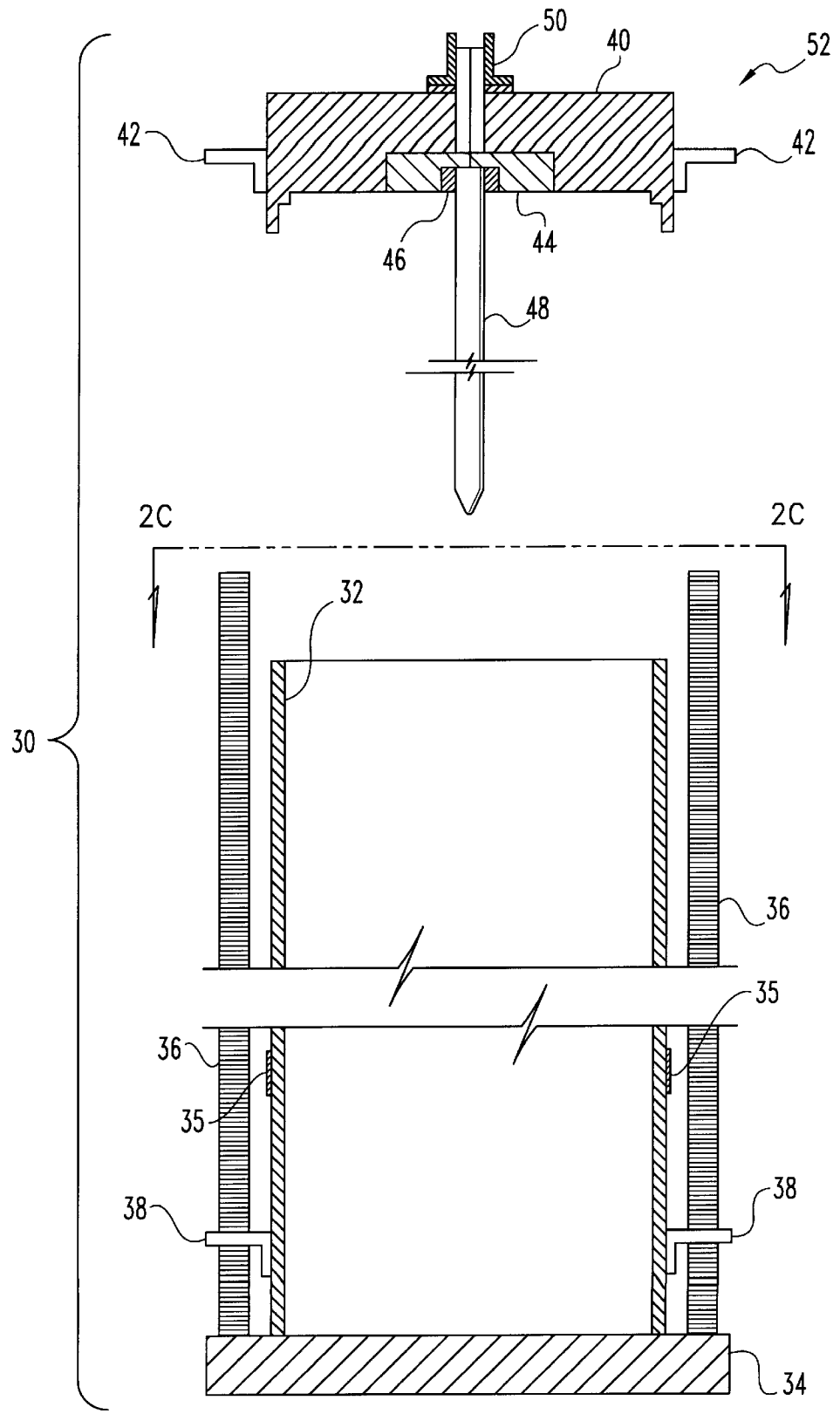
FIGS. 2A–B illustrate various components of a cylindrical cell of the present invention.

The cylindrical cell 30 of FIG. 2A forms a coaxial transmission line for measuring the moisture content of a sample of soil removed from the ground. The cylindrical cell 30 includes a cylindrical tube 32 which holds the soil sample and acts as the outer conductor of the coaxial transmission line. The tube 32 is preferably formed from a thin conductive metal, such as stainless steel, and preferably includes a longitudinal cut which creates a small gap running the length of the tube 32. Before compacting soil in the tube 32, hose clamps of the like (not shown) are used to close the gap around the soil sample. The gap aids in removal of the soil from the tube 32 after testing is complete. Stability is provided during testing by a non-conductive base 34 having two or more bolts 36 mounted thereto. The tube 32 is coupled to the bolts 36 by means of flanges 38 welded (or otherwise coupled) to the tube 32. Nuts (not shown) may be threaded onto the bolts 36 to bear down upon the flanges 38.

The cylindrical cell (CC) 30 further comprises a coaxial interface cap 40 which also mounts onto the bolts 36 by means of flanges 42 welded (or otherwise) coupled to the interface cap 40. Nuts (not shown) may be threaded onto the bolts 36 to bear down upon the flanges 42. The interface cap 40 is made of a conductive material, such as stainless steel. The lower central portion of the interface cap 40 contains a non-conductive insert 44, which is preferably formed of plastic. Insert 44 further contains a second threaded metal insert 46 therein. A center rod 48 screws into the threaded metal insert 46 and forms the center conductor of the coaxial transmission line of the cylindrical cell (CC) 30. The rod 48 could alternatively be threaded directly into the plastic insert 44, but this reduces the durability of the cap 40 for repeated use. The coaxial cable 18 of a TDR instrument 20 may be coupled to the tube 32 and center rod 48 by means of the connector 50 mounted to the interface cap 40. The interface cap 40/rod 48 assembly is hereinafter referred to a the coaxial assembly (CA) 52.

Figure 2B:
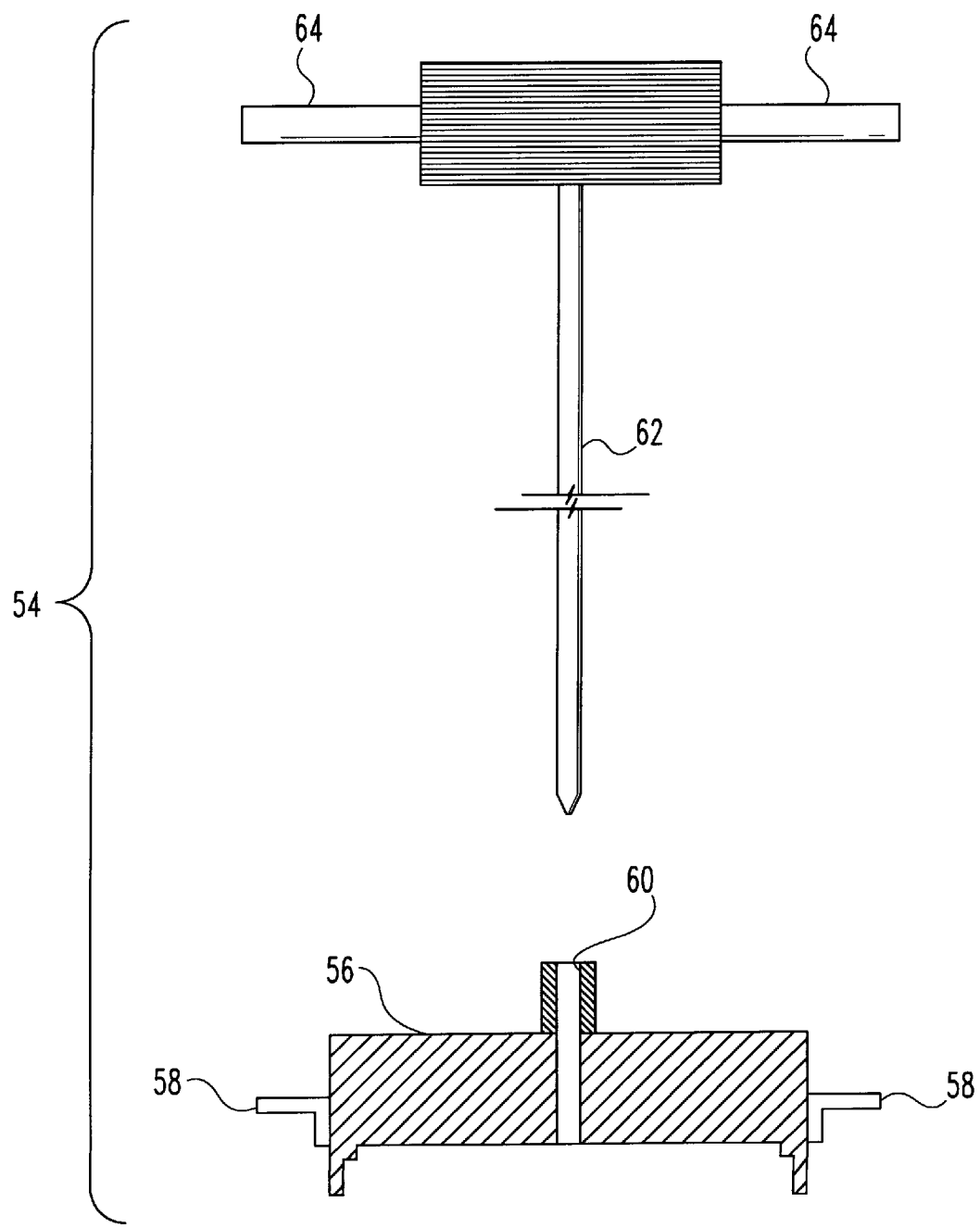

Insertion of the coaxial assembly (CA) 52 into hard soil samples is facilitated by the hand penetrometer 54 and template 56 of FIG. 2B. After the soil sample has been compacted into the tube 32, the template 56 is attached to the top of the tube 32 by means of the flanges 58 and the bolts 36. Once mounted, the central hole 60 of the template 56 is directly over the longitudinal axis of the tube 32. The rod 62 of the hand penetrometer 54 is then inserted into the soil through the hole 60. Downward pressure on the rod 62 may be exerted by pressing upon the handles 64. Once the rod 62 has been fully inserted through the hole 60, it is withdrawn completely. This leaves a central shaft through the soil sample in the tube 32 which is perfectly aligned to receive the central rod 48 of the coaxial apparatus (CA) 52. The template 56 is then removed from the tube 32 and the coaxial apparatus (CA) 52 is mounted to the tube 32, completing the cylindrical cell (CC) 30. Use of the hand penetrometer 54 reduces the stress applied to the CA 52 with repeated use. Use of the hand penetrometer 54 with the template 56 further assures that the central rod 48 of the CA 52 is inserted directly along the longitudinal axis of the CC 30, which is very important for accurate measurements.

Step-by-step procedures for performing a test with the CC 30 are as follows:

1. The tube 32 is placed on the base plate 34 and fastened to it.
2. A representative quantity of soil sufficient to fill the tube 32 is taken from the in-place measurement site. For measuring in-filed moisture content, the soil is dig out from the ground where measurement is required. Then the soil is compacted in layers using a tamping rod.
3. The weight of the tube 32 with soil in it is measured using an electronic balance to measure the wet density of the compacted soil in the tube 32.
4. The template 56 is placed on top of the tube 32 and the hand penetrometer 54 is used to make a hole along the center line (longitudinal axis) of the soil specimen.
5. The template 56 is removed and the rod 48 of the CA 52 is pushed through the hole in such a way that it does not move laterally while pushing. Fingers of one hand are placed on the surface around the rod 48 to act as a guide for the rod 48 to resist any lateral movement of it while the other hand is used to push the CA 52 in the hole. Any air gap that appears around the rod 48 near the top surface is closed by pressing the soil against the rod 48.
6. When the cap 40 of the CA 52 sits on top of the tube 32, connection is made with the TDR equipment 20 and a reading is taken which gives the dielectric constant of the soil.
7. The rod 48 is removed from the tube 32 by pulling the cap 40 out of the soil sample.

This device and the the above procedures provide the wet density of the soil in the tube 32 and its dielectric constant.

Figure 3:
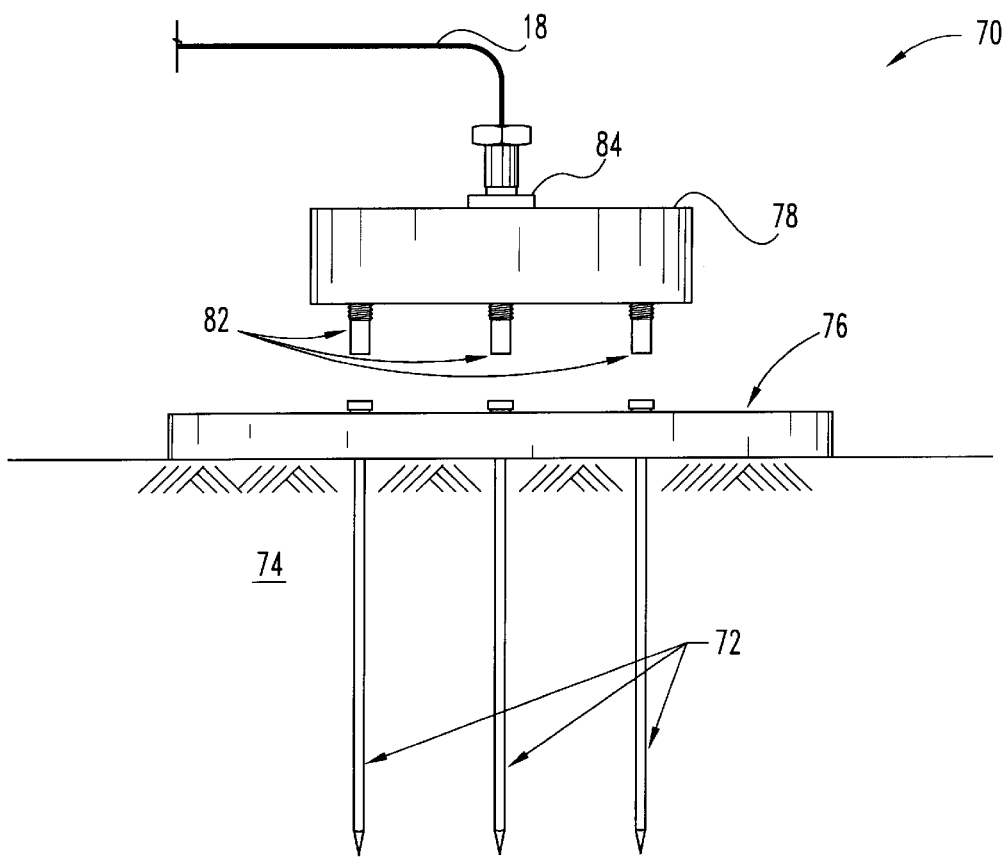
FIG. 3 is a side elevational view of a first embodiment multiple rod probe of the present invention, illustrated in use with a template and spikes of the present invention.
Figure 4:
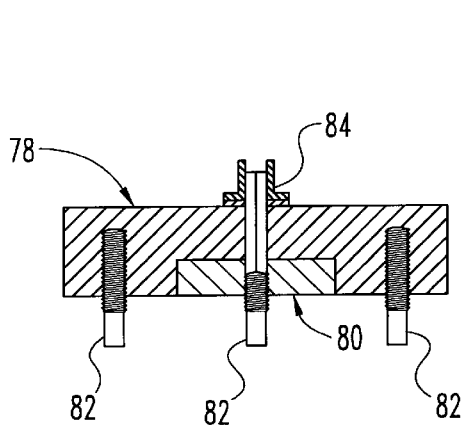
FIG. 4 is a cross-sectional view of the first embodiment multiple rod probe of FIG. 3.
Figure 5:
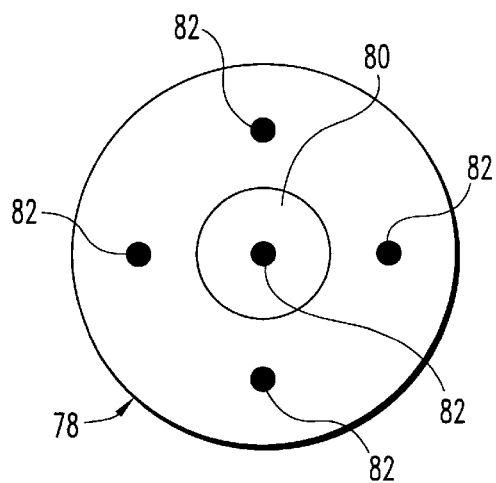
FIG. 5 is a bottom plan view of the first embodiment multiple rod probe of FIG. 3.

The multiple rod probe (MRP) 70 of the present invention is illustrated in FIGS. 3–5. The multiple rod probe (MRP) 70 is used to measure the dielectric constant (and hence the volumetric moisture content) of an in-place soil sample. The design of the multiple rod probe (MRP) 70 is such that it separates the conducting rods that are driven into the soil from the interface cap which is coupled to the TDR equipment 20. In conventional probes, such as the probe 10 of FIG. 1, the conducting rods 12, 14 are permanently connected to the interface cap. As illustrated in FIG. 3, the connection between the rods and the interface cap is not permanent with the multiple rod probe (MRP) 70 of the present invention. The conducting rods 72 of the MRP 70 are driven into the soil 74 using a template 76 placed upon the surface of the soil 74 as a guide. It is extremely important that the rods 72 be driven into the soil 74 in such a way that they fit the soil 74 tightly. Any gap around the rods 72 will give erroneous results. The template 76 is preferably formed from wood or steel and includes guide holes through which the rods 72 are driven into the soil 74 in a predetermined pattern. This pattern includes a centrally located rod and tow or more peripherally located rods, all being equidistant from the central rod. The rods 72 are preferably common metal spikes, and extend into the soil 74 to a depth of approximately 9 inches. The template 76 is removed after the rods 72 have been driven into the soil 74.

The multiple rod probe (MRP) 70 further includes an interface cap 78 which is formed from a conductive material, such as stainless steel. As shown in the cross-sectional view of FIG. 4 and the bottom view of FIG. 5, the cap 78 includes a central annular non-conductive insert 80, which is preferably formed of plastic. The cap 78 has a plurality of threaded studs 82 threadingly engaged therewith. The centrally located stud 82 is threaded into the non-conductive insert 80, while the peripheral studs are threaded directly into the conductive portion of the cap 78. A coaxial connector 84 is mounted to the cap 78 in such a way that the outer conductor of the coaxial connector 84 contacts the conductive portion of the cap 78 (and therefore the peripherally located studs 82), while the center conductor of the connector 84 contacts the centrally located stud 82 but is insulated from the conductive portion of the cap 78. The connector 84 is coupled to a TDR instrument 20 by means of a coaxial cable 18.

In order to use the multiple line probe (MRP) 70, the template 76 is placed on the surface of the ground at a location where it is desired to measure the dielectric content of the soil 74. The spikes 72 are then driven into the soil 74, using the template 76 as a guide. Once the spikes 72 have been driven into the soil 74, the template 76 is removed and the cap 78 is positioned on top of the spikes 72 such that the studs 82 make contact with each of the spikes 72. If any of the studs 82 do not touch the corresponding head of the spikes 72, the length of the stud 82 may be adjusted by turning the stud 82 until proper connection is established. Thus configured, the MRP 70 is, in fact, a combination of two transmission lines. The first segment has air as the dielectric medium, and the second segment has soil as the dielectric medium. As the air has a very low dielectric constant compared to moist soil, a distinctive discontinuity in the reflected signal will appear at the air-soil interface. This will facilitate proper measurement of the dielectric constant of the soil 74.

The present invention achieves an advantage over the prior art probe 10 of FIG. 1 by completely separating the in-ground spikes 72 from the measurement cap 78. The robust spike 72 may be repeatedly driven into hard soil without creating any wear and tear upon the cap 78. In fact, the spike 72 may be driven into soils (using a hammer) into which the prior art probe 10 could not be inserted. The MRP 70 therefore facilitates making many measurements of soil at different locations, whereas the prior art probe 10 of FIG. 1 is normally permanently mounted at a location and repeated measurements are made at the same location.

Figure 6:
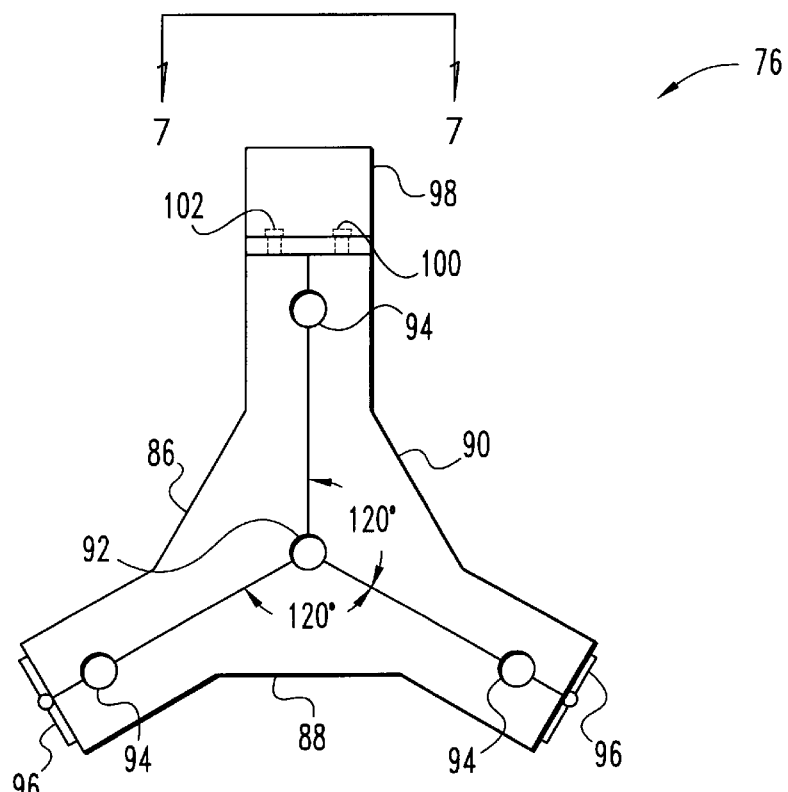
FIG. 6 is a first embodiment hinged template of the present invention.
Figure 7:
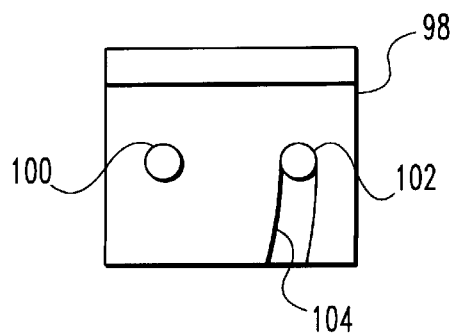
FIG. 7 is a side elevational view of a releasable coupling of a first embodiment hinged template of FIG. 6.
Figure 8:
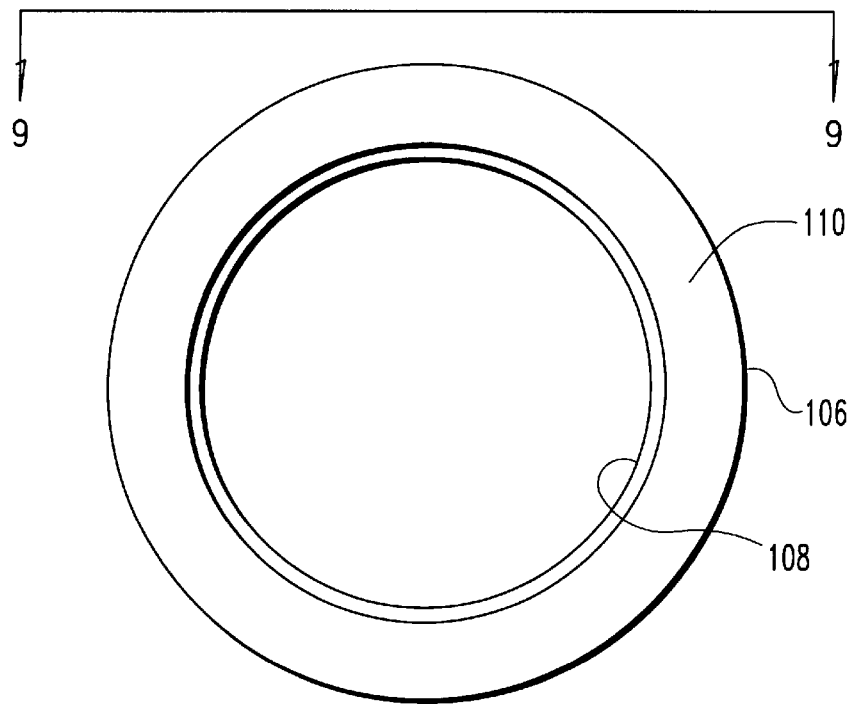
FIG. 8 is a top plan view of a conductive ring of the present invention for allowing the multiple rod probe of the present invention to be used with the cylindrical cell of the present invention.
Figure 9:
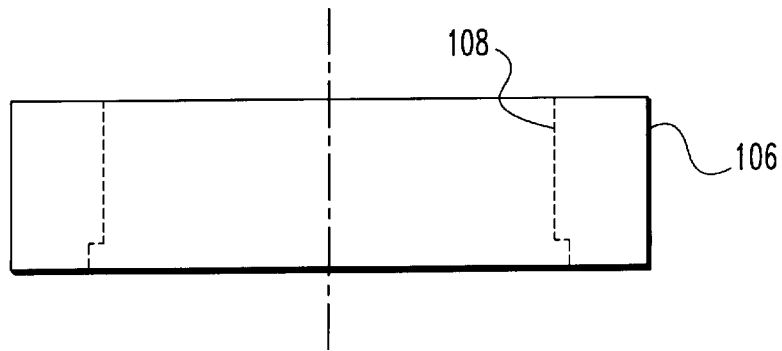
FIG. 9 is a side elevational view of the conductive ring of FIG. 8.

A preferred embodiment of the template 76 for use with the MRP 70 is illustrated in plan view in FIG. 6. The template 76 of FIG. 6 is intended for use with an MRP having one central probe and three peripheral probes. Those skilled in the art will recognize that the design of the template 76 of FIG. 6 may be readily altered to accommodate an MRP 70 having a fewer or greater number of peripheral probes. The template 76 is formed from three identical pieces of stainless steel 86, 88 and 90. The pieces 86–90 fit together in the manner shown, and define a central hole 92 and three peripheral holes 94 therebetween. The piece 86 is coupled to the piece 88 by means of a hinge 96, and the piece 88 is coupled to the piece 90 by means of a second hinge 96. The hinges 96 allow the pieces 86–90 to be unfolded away from the spikes 72 after they have been driven into the soil 74. Such removal of the template 76 is necessary when the heads of the spike 72 have a greater diameter than the holes 92 and 94. The template 76 is held in its closed position by means of a block 98, a screw 100 and a screw 102. As shown in the end view of FIG. 7, the block 98 is rotatably mounted to the piece 90 by means of the screw 100. The screw 102 is engaged by the clock 98 by means of a slot 104. The block 98 may be disengaged from the screw 102 by rotating the block 98 counterclockwise about the screw 100. The slot 104 allows passage of the block 98 around the screw 102. Once the block 98 has been disengaged from the screw 102, the pieces 86–90 may be folded away from each other in order to release the template 76 from the spikes 72.

In an alternative embodiment of the present invention, the cap 78 of the MRP 70 may be used to replace the CA 52 of the cylindrical cell (CC) 30. In order to do this, the hand penetrometer 54 and the template 56 are used to create a central bore through the soil sample, as with the first embodiment. A spike 72 is then inserted into this central bore. The spike 72 will make contact with the central stud 82 of the cap 78. In order to provide contact between the peripheral studs 82 of the cap 78 and the outer surface of the tube 32, the ring 106 is placed over the top of the tube 32. The ring 106 is made from a conductive material, such as stainless steel. The ring 106 contains a central opening 108 which allows the central stud 82 of the cap 78 to contact the spike 72. However, the ring 106 further includes a flat annular section 110 which is wide enough to make contact with the peripheral studs 82 of the cap 78. The ring 106 therefore provides conductive contact between the peripheral studs 82 of the cap 78 and the shell of the tube 32. By using the cap 78 as the measurement device for the cylindrical cell (CC) 30, instead of the purpose-built coaxial assembly (CA) 52, only a single measurement device is required for both the cylindrical cell (CC) 30 and the multiple rod probe (MRP) 70. Furthermore, use of the cap 78 with both devices facilitates uniformity among measurements made with both devices.

Therefore, use of the multiple rod probe (MRP) 70 allows measurement of in-place soil dielectric constant (which yields θ of the soil in-place). Use of the cylindrical cell (CC) 30 measures θ of the soil sample within the cylindrical cell as well as the wet density of the soil within the CC 30. The gravimetric moisture content w of the soil in the CC 30 may then be computer. As discussed hereinbelow, this gravimetric moisture content of the soil within the CC 30 may be used to calculate the in-place soil density from the measured in-place volumetric moisture content, θ.

The coaxial apparatus CA 52 measures θ in the cylindrical cell (CC) and the multiple rod probe (MRP) 70 measures θ of soil in-place. The gravimetric moisture content of soil in the CC 30 is measured using the measured density of soil in the CC 30. This gravimetric moisture content can be used to calculate the in-place density from the measured in-place volumetric moisture content, θ. From the Eq. 5, moisture content, w, can be expressed in terms of total density, $\rho_t$, and $$w = \frac{\theta}{\rho_t/\rho_w - \theta} \tag{8}$$

So, $$w_{cc} = \frac{\theta_{cc}}{(\rho_t)_{cc}/\rho_w - \theta_{cc}} \tag{9}$$

where: $w_{cc}$, $\theta_{cc}$, and $(\rho_t)_{cc}$ are the gravimetric moisture content, volumetric moisture content and total density of the soil in the CC 30, respectively. Also $$w_{insitu} = \frac{\theta_{insitu}}{(\rho_t)_{insitu}/\rho_w - \theta_{insitu}} \tag{10}$$

where: $w_{insitu}$, $\theta_{insitu}$, and $(\rho_t)_{insitu}$ are the gravimetric moisture content, volumetric moisture content and the total density of the soil in-place, respectively. Since the soil in the CC 30 is quickly taken from in-place, it can be assumed that $$w_{insitu} = w_{cc} = w \tag{11}$$

Therefore, $$w = \frac{\theta_{cc}}{(\rho_t)_{cc}/\rho_w - \theta_{cc}} \tag{12}$$

Equating right hand sides of Eqs. 9 & 10, we get $$(\rho_t)_{insitu} = (\rho_t)_{cc} \frac{\theta_{insitu}}{\theta_{cc}} \tag{13}$$

Equations 12 and 13 give in-place moisture content and total density of soil. In-place dry density can be calculated from total density using the measured moisture content as $$(\rho d)_{insitu} = \frac{(\rho_t)_{insitu}}{1+w} \tag{14}$$

where $(\rho d)_{insitu}$ is the dry density of in-place soil. The unit weight of soil can be calculated from the density as $$(\gamma_t)_{insitu} = (\rho_t)_{insitu} g \tag{15}$$

and $$(\gamma_d)_{insitu} = (\rho_d)_{insitu} g \tag{16}$$

where $(\gamma_t)_{insitu}$ and $(\gamma_d)_{insitu}$ are the total unit weight and the dry unit weight of in-place soil respectively, and g is the acceleration due to gravity. The accuracy of measuring total density would be better than that of dry density as evident from Eq. 14. Any error in measuring gravimetric moisture content, w, using the CC 30 contributes for the higher error in measuring dry density compared to the error involved in measuring total density.

To access the performance of Eq. 13 in measuring in-place density, it is necessary to compare it with conventional measured density. Also it is necessary to test the performance of Eq. 13 for many possible parameters. Laboratory experiments using cylindrical cells (CC) 30 can be conducted to achieve these goals. If two soil specimens are prepared at the same moisture content, w, in two cylindrical cells (CC) 30, then the density of one of the specimens can be measured using the density of the other specimen using $$\rho_{t\,cc2} = \frac{\theta_{cc2}}{\theta_{cc1}} \rho_{t\,cc1} \quad (17)$$

The density thus measured can be compared with the conventionally measured density of the soil specimen.

An experimental program was undertaken to assess the performance of the CC 30 in measuring moisture content, and to develop the procedure for measuring in-place density of soil. The development of the procedure for determining in-place density required determination of dielectric constants of soil specimens having the same moisture contents but having different dry densities. Using the CC 30 was most easy and ideal for that purpose. Experiments with the CC 30 to develop $K^{0.5}$–$\rho_d$ relationships provided the opportunity to assess the performance of the CC 30 in measuring in-place moisture content and to develop the procedure for measuring density. A wide range of parameters, i.e. soil type, moisture content, density, etc. were covered in the experiments using the CC 30. To assess the performance of the developed procedure for measuring density, field experiments were conducted using the MRP 70 and the CC 30. The prior art sand-cone method was used to measure in-place density to compare with the in-place density measured by the present technique. As there is no exact prior art method of measuring in-place density to correctly assess the performance of the method of the present invention, it was necessary to conduct experiments in the laboratory under simulated filed conditions to correctly assess the performance of measuring in-place density.

Figure 2C:
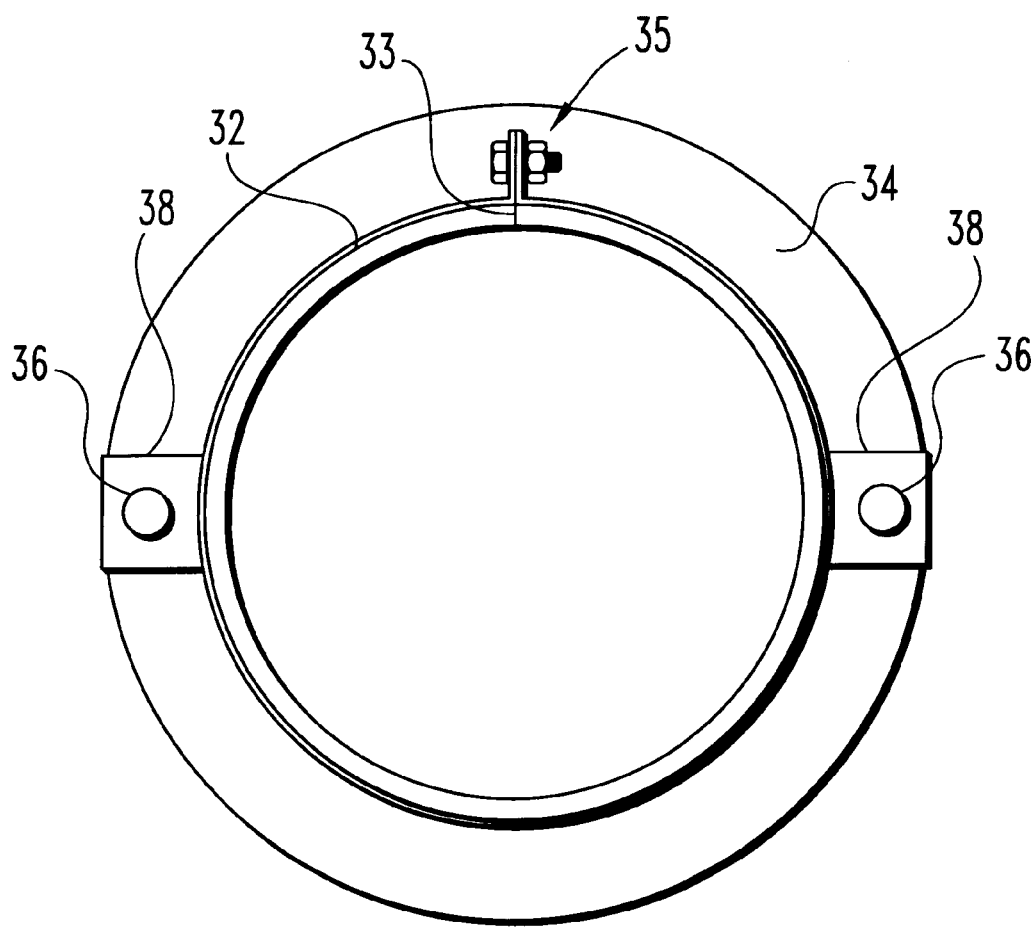

The CC 30 shown in FIG. 2 was used for laboratory experiments. Important dimensions of the device were: effective length of probe, L=28.6 mm; diameter of probe rods, d=4.76 mm; inside diameter of CC, $D_i$=72.6 mm; outer diameter of CC, $D_0$=76.2 mm.

The main steps for the laboratory experiment were:

1. Prepare the soil at a specified moisture content.
2. Compact the soil in two coaxial cells (CC's) 30 in a way that soil in each cell has a different density. Specimens should be prepared in a way that the moisture content of each specimen remains the same.
3. Measure the dielectric constants of the specimens using the CA 52.
4. Measure the wet-densities of specimens in each cell 30. Take a sample from each cell 30 for measuring moisture content by the prior art oven drying method. Use oven drying moisture content to calculate dry densities.
5. Compute gravimetric moisture content of soil in each cell 30 using the measured dielectric constant and wet density. Compute dry density (with Eq. 14) using this gravimetric moisture content.
6. Use the dry density of one of the specimens measured in step (5) to measure the dry density of the other specimen using Eq. 17. Compare this density with that calculated in step (4).
7. Compare the gravimetric moisture content computed in step (5) with the oven drying moisture content.
8. Prepare additional pairs (at least four) of specimens with the soil prepared at the same moisture content used in step (1), but with different compacting efforts. Densities of the specimens should cover the whole range of normal densities (loosest to densest). Also the difference in density between the specimens in each pair should cover all possible ranges. Repeat steps (1) to (6) for soil prepared at other moisture contents to cover a wide range of moisture content.

TABLE 1

SOIL CHARACTERISTICS

| Soil Type | % Sand | % Silt | % Clay | Range density (Mg/m³) | Range moisture content (%) |
|---|---|---|---|---|---|
| Crosby till | 5 | 15 | 80 | 1.05–1.55 | 12–27 |
| Silt | 0 | 100 | 0 | 1.2–1.6 | 4–24 |
| Fine Sand | 100 | 0 | 0 | 1.4–1.68 | 1.2–13.0 |
| Kaolinite | 0 | 0 | 100 | 1.0–1.45 | 6–28 |
| Cherry L. Soil | 5 | 70 | 25 | 1.3–1.65 | 8–24 |

For field experiments, the MRP 70 of FIG. 3 and the CC 30 of FIG. 2 were used. The key dimensions of the MRP 70 were: effective length of probe, L=230 mm; diameters of probe rods, d=7.9 mm; spacings of the inner to the outer rods, s=37 mm. The main steps for the field experiments were:

1. Use the MRP 70 to measure in-place dielectric constant of soil.
2. Dig out a sufficient quantity of soil from the place of in-place measurement and compact it in a number of CC's 30 at different densities (loosest to densest). Measure the dielectric constants of the soil in each of these CC's 30. The soil to be used in each CC 30 should be taken uniformly over the depth of MRP 70 insertion.
3. Measure the wet density of the soil in the CC 30. Compute the volumetric and the gravimetric moisture content of the soil in the CC 30 from the dielectric constant and measured densities (using Eq. 6 and 9). Calculate the dry density of the soil with the calculated gravimetric moisture using Eq. 14.
4. Relate the dry density of the soil in the CC 30 to the dry density of the soil in-place using the Eq. 13.
5. Measure the wet density of the soil at the place of in-place measurement by the prior art sand cone method.
6. Take a sample for measuring moisture content by the prior art oven drying method. Compute the dry density from the wet density measured by the prior art sand cone method. Compare this dry density with that found in step (4).
7. Compare the moisture content measured by TDR method with that measured by oven drying method.

The simulated field experiment was conducted in the laboratory using the same devices as those that were used for the field experiments. The only difference was that the solid whose in-place density and moisture content was to be measured was the soil compacted in a large mold. The MRP 70 was installed in the central area of the soil in the mold. The main steps of the method were:

1. Prepare the soil at a desired moisture content and compact the soil in a big compaction mold (6 inch diameter, 9 inch height).
2. Use the MRP 70 to measure the in-place dielectric constant of the soil. The length of the conductors 72 should be little more than 9 inch (about 10 inch).
3. Measure the wet density of the soil in the mold.
4. Take soil from the mold to measure the dielectric constant in the CC 30. Measure the wet density of the soil in the CC 30 and compute volumetric moisture content (Eq. 6), gravimetric moisture content (Eq. 9), and dry density (Eq. 14) of the soil. Compute the dry density of the soil in the mold using this information (Eq. 17). Take a sample of soil for measuring moisture content by the prior art oven drying method.

5. Repeat step (4) to perform at least 5 more tests. Each time compact the soil in the CC 30 at a different density to cover a wide range of densities (loosest to densest).
6. Compute the actual dry density of the soil in the mold from the measured wet density and the prior art oven dry moisture content.
7. Compare the measured dry density and the moisture content with the actual dry density and the prior art oven dry moisture content.
8. Repeat the whole procedure for soils prepared at other moisture contents to cover a wide range of moisture content.

Eq. 6 and Eq. 8 were used to compute gravimetric moisture contents from the measured dielectric constants. A very good correlation ($R^2=0.96$) is obtained between the actual and the measured moisture contents. The standard error of measurement is 0.013. The error involved in moisture content measurement using Eq. 6 is higher for clayey soil compared to cohesionless soil, as expected. These findings prove the validity of the design and procedures involved in measuring moisture content using the cylindrical cell (CC) 30.

To obtain a calibration equation of the form of Eq. 7, values of $K^{0.5}$ were plotted with actual volumetric moisture contents. The result of regression analysis on this data is: $K^{0.5}=1.5+8.4\,\theta$. To obtain soil specific calibration equations, regression analyses were carried out for each soil type measured in this study. Table 2 gives the coefficients of regression analyses and values of $R^2$. The values of intercepts vary from 1.14 to 1.58, values of slopes vary from 8.26 to 9.78, correlation coefficients vary from 0.967 to 0.988. From these results it is clear that a common calibration equation may not be applicable for all soils. Soil specific calibration equations are necessary for accurate results. Using these soil specific calibration equations, soil moisture contents were back calculated. The standard error of measurement for this data is 0.008, less than what was obtained using Eq. 6.

TABLE 2

REGRESSION ANALYSIS: $K^{0.5} = c_1 + c_2\theta$

| Soil Type | Intercept, $c_1$ | Slope, $c_2$ | $R^2$ |
|---|---|---|---|
| Crosby till | 1.14 | 9.78 | 0.967 |
| Silt | 1.56 | 8.74 | 0.989 |
| Fine Sand | 1.59 | 8.263 | 0.987 |
| Cherry Lane | 1.31 | 8.96 | 0.988 |
| Kaolinite | 1.59 | 8.30 | 0.989 |

In order to measure density from the dielectric constant, it is necessary to establish the relationship between $K^{0.5}$ and density. From Eq. 7 it is seen that a linear relationship exists between $K^{0.5}$ and $\theta$. It is also likely that a linear relationship might exist between $K^{0.5}/\rho_d$ and w. Regression analysis for the $K^{0.5}/\rho_d$–w relationship was carried out for each soil type and the result is shown in Tab. 3. This table shows that an excellent linear relationship exists between $K^{0.5}/\rho_d$ and w. comparing Tab. 3 and Tab. 2, it is seen that a better linear relationship exists between $K^{0.5}/\rho_d$ and w than the linear relationship between $K^{0.5}$ and $\theta$ for almost all soil types. From Tab. 3, it is seen that the values of intercept a are close to 1 for all soils except kaolinite, for which is is 1.57. Similarly, the values of slope b are in the range of 8 to 9 except for kaolinite for which it is 6.79. From this data, it is obvious that a common calibration equation may not be suitable for all soil types. There is excellent linear correlation between $K^{0.5}/\rho_d$ and w for different types of soil. This observation shows that soil specimens having the same gravimetric moisture content have the same value for the ratio of $K^{0.5}/\rho_d$. To see whether the ration $(K^{0.5}-c)/\rho_d$ has a better correlation with w than the $K^{0.5}/\rho_d$–w correlation, they were plotted for different values of c ranging from 0 to 1. Table 4 shows the results of the regression analyses. It is seen that $R^2$ is not very sensitive to the values of c ranging from 0 to 1. For simplicity, c=0 was chosen and $K^{0.5}/\rho d$–w relationship was used for measuring density. From these results it can be concluded that $$\frac{K^{0.5}}{\rho d} = a + bw \qquad (18)$$

where, depending on soil type, a may vary from 0.95 to 1.6 and b may vary from 6.5 to 9.5.

TABLE 3

REGRESSION ANALYSIS: $K^{0.5}/\rho_d = a + bw$

| Soil Type | Intercept, a | Slope, b | $R^2$ |
|---|---|---|---|
| Crosby till | 0.978 | 9.17 | 0.947 |
| Silt | 1.102 | 8.178 | 0.993 |
| Fine Sand | 1.034 | 7.96 | 0.992 |
| Cherry Lane | 0.993 | 8.65 | 0.995 |
| Kaolinite | 1.576 | 6.79 | 0.998 |

TABLE 4

REGRESSION ANALYSIS: $(K^{0.5} - c)/\rho_d = a + bw$

| c | a | b | $R^2$ |
|---|---|---|---|
| 0 | 1.007 | 8.081 | 0.985 |
| 0.3 | | | 0.987 |
| 0.5 | 0.682 | 8.63 | 0.987 |
| 0.7 | | | 0.986 |
| 1.0 | 0.356 | 8.447 | 0.982 |

From Eq. 18 we get $$\frac{K_1^{0.5}}{K_2^{0.5}} = \frac{\rho_{d1}}{\rho_{d2}} \qquad (19)$$

where $K_1$, $K_2$ and $\rho_{d1}$, $\rho_{d2}$ are the dielectric constants and dry densities of two soil specimens having the same moisture content w. Equation 19 can be written as $$R_K = R_d \qquad (20)$$

where $R_K$ and $R_d$ are the ratio of refractive indices ($K^{0.5}$'s) and ratio of densities (dry or total), respectively. Equation 18 may be used for measuring gravimetric moisture content as $$w = \frac{K^{0.5} - a\rho_t}{b\rho_t - K^{0.5}} \quad (21)$$

Equation 21 was used with the appropriate values of a and b taken from Table 4 for computing w. Measured and actual moisture contents were compared. The standard error of measurement is 0.0075, which is less than that obtained using Eq. 6 or Eq. 7. The data are given in Tab. 5.

TABLE 5

REGRESSION ANALYSIS: $w_{measured} = a + bw_{actual}$

| Eq. used | a | b | $R^2$ | S.E.(%) |
|---|---|---|---|---|
| Eq. 6 | 0 | 0.97 | 0.96 | 1.21 |
| Eq. 7 | 0 | 1.00 | 0.985 | 0.784 |
| Eq. 16 | 0 | 0.999 | 0.985 | 0.750 |

Dielectric constants of soil specimens having the same w were measured in the laboratory using the CC 30. Eq. 19 was used to compute the density of one specimen using its dielectric constant and the density and the dielectric constant of another specimen. Since dry density is computed from the measured total density and w, any in measuring w would affect accuracy of measuring density.

To correctly access the performance of Eq. 19 in measuring density, it would be better to compute total density and compare it with actual total density, this isolating the effect of w on density measurement. Measured and actual total densities were plotted against one another and showed reasonably good correlation between the measured and actual densities; slope very close to 1, intercept very close to zero, and high correlation coefficient. The standard error of measurement is 0.0307 Mg/m³. The gravimetric moisture contents were used to compute the dry densities and these were compared with the conventionally measured dry density. The standard error is 0.032 Mg/m³, slightly higher than that for total density, because of the error involved in measurement of gravimetric moisture content.

Plots of measured vs. actual total densities showed that there is scatter in the data. To increase the accuracy of the density measurement, it is necessary to identify the factors that affect the density measurement accuracy. Probable factors that might affect the accuracy of measurement are: $R_d$, moisture content, density, etc. Percent error in density measurement was plotted with $R_d$ and did not show any remarkable trend of influence of $R_d$ on percent error. But for some soil types, high $R_d$ ($R_d > 1.1$) may increase the error involved in the density measurement. Percent error was plotted with moisture content and, as expected, accuracy increases with increase in moisture content.

The reason for higher error involved in measuring dry density from total density is because of the error involved in measuring moisture content. The additional error in measuring dry density compared to that of total density would be lower at higher moisture contents and when the error involved in moisture content measurement is small.

Figure 10:
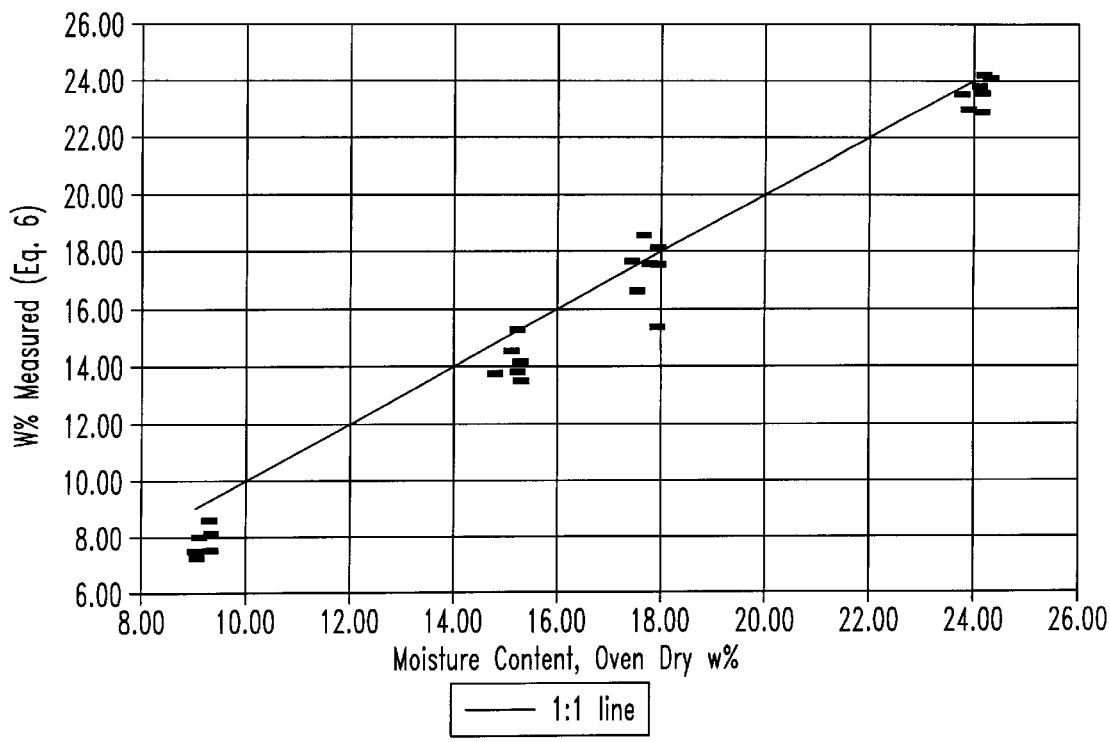
FIG. 10 is a graph of gravimetric moisture content as calculated by Eq. 6 and by a prior art oven dry method.
Figure 11:
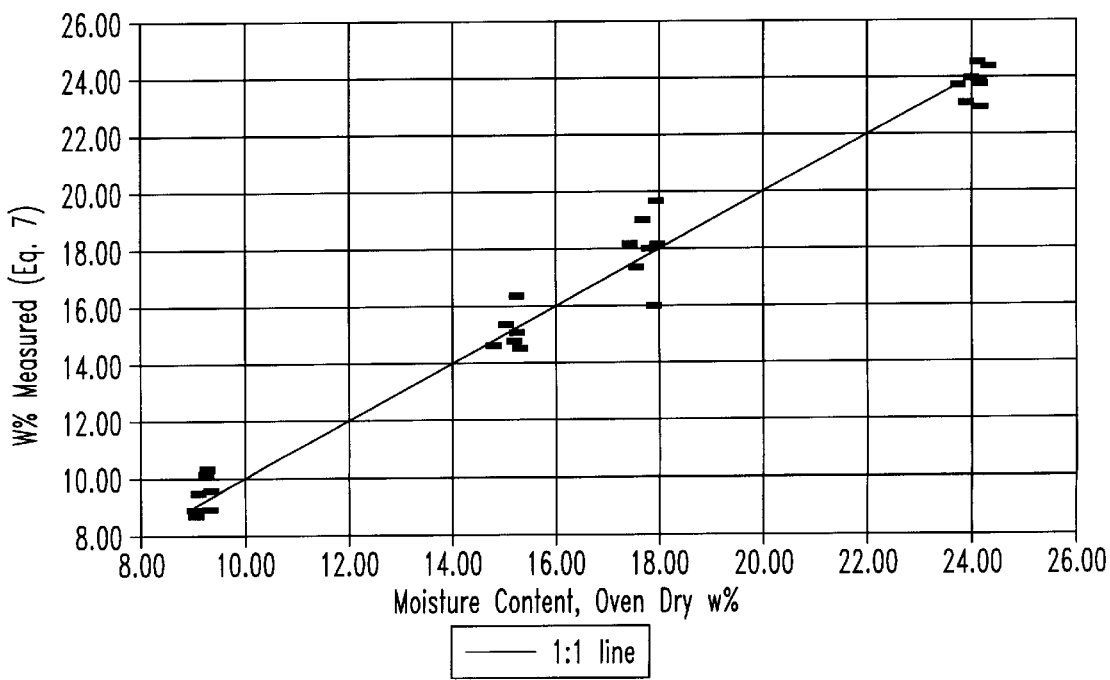
FIG. 11 is a graph of gravimetric moisture content as calculated by Eq. 7 and by a prior art oven dry method.
Figure 12:
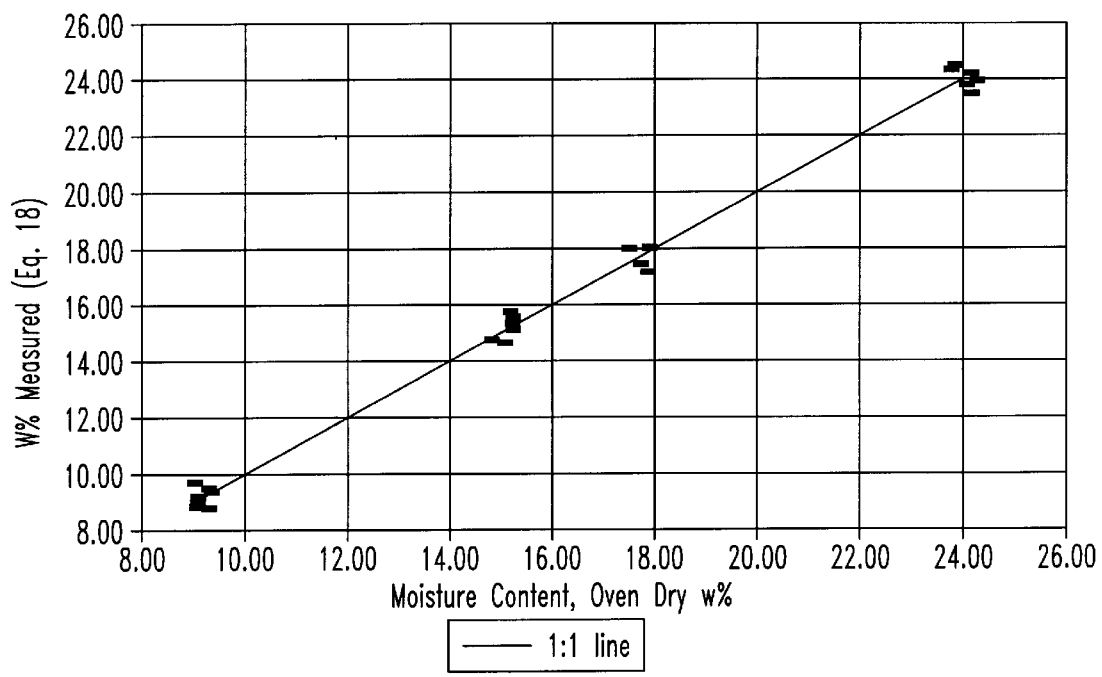
FIG. 12 is a graph of gravimetric moisture content as calculated by Eq. 18 and by a prior art oven dry method.

The procedure developed was used to measure in-place density and moisture content using the MRP 70 and the CC 30. Because it is difficult to conduct field experiments over widely varying moisture content and density conditions for a given soil, experiments were first conducted in he laboratory under simulated field conditions. The soil used for the simulated field experiment was the Cherry L. Soil. Densities were measured using Eq. 19. The measured density and the conventionally measured density were plotted. The measured and the actual density follow a 1:1 line. The standard error of measurement is only 0.020 Mg/m³, much less than what was obtained from the laboratory experiments. Percent error in density measurement was plotted with $R_d$ and w and this data showed that the maximum error in density measurement is about 3%. No noticeable trend of influence of $R_d$ on measurement accuracy is observed. But the error measurement reduces as w increases. The measured gravimetric moisture contents using three different equations are shown in FIGS. 10, 11 and 12. Eq. 6 gives the least accurate result (FIG. 10) compared to Eq. 7 plotted in FIG. 11 and to the new Eq. 18, which gives the best result (FIG. 12) with slope exactly equal to 1, intercept equal to 0 and $R_2$ of 0.995. Dry densities computed using measured moisture contents using the new equation (as shown in FIG. 12) showed a standard error of measurement of dry density to be a very low 0.021 Mg/m³. these results prove the validity of the procedure and Eq. 18 developed for measuring density and moisture content.

Field experiments were conducted at a local field site know as Cherry Lane (the site soil was identified as Cherry L. Soil in Tab. 1). Density was compared with the density measured by the prior art sand-cone method. The maximum variation of the measured density using the present method is about 3%. Over a wide range of $R_d$, the measurement accuracy is consistent irrespective of the value of $R_d$. These results prove the validity of the procedure developed in the laboratory for measuring in-place density and moisture content.

While the invention has been illustrated and described in detail in the drawings and foregoing description, the same is to be considered as illustrative and not restrictive in character, it being understood that only the preferred embodiment has been shown and described and that all change and modifications that come within the spirit of the invention are desired to be protected.

What is claimed is:

1. A method of installing an apparatus for measuring a dielectric constant of an in-place soil sample, comprising the steps of:

(a) providing a template having a central hole therethrough and a plurality of peripheral holes therethrough, the plurality of peripheral holes being substantially equidistant from the central hole;

(b) laying the template on a surface of the in-place soil sample;

(c) driving a plurality of conductive spikes into the soil through the central hole and each of the peripheral holes of the template;

(d) removing the template;

(e) providing a probe head, comprising:
an annular conductive body;
a plurality of conductive peripheral studs mounted to a bottom surface of the body;
a conductive central stud; and
an annular non-conductive insert coupling the body to the central stud;
wherein a first spacing between the central stud and the peripheral studs is substantially the same as a second spacing between the central hole and the peripheral holes, such that each stud is aligned with a respective spike when the probe head is placed over the spikes after they have been driven into the soil sample; and (f) placing the probe head onto the conductive spikes, such that each stud is aligned with a respective spike.

2. A method of installing an apparatus for measuring a dielectric constant of an in-place soil sample, comprising the steps of:
   (a) providing a template having a central hole therethrough and a plurality of peripheral holes therethrough, the plurality of peripheral holes being substantially equidistant from the central hole;
   (b) laying the template on a surface of the in-place soil sample;
   (c) driving a plurality of conductive spikes into the soil through the central hole and each of the peripheral holes of the template; and
   (d) removing the template.

3. A method of installing an apparatus for measuring a dielectric constant of an in-place soil sample, comprising the steps of:
   (a) providing a probe head, comprising:
      an annular conductive body;
      a plurality of conductive peripheral studs mounted to a bottom surface of the body;
      a conductive central stud; and
      an annular non-conductive insert coupling the body to the central stud;
      wherein the central stud and the peripheral studs are arranged in a first pattern;
   (b) driving a plurality of conductive spikes into the soil, wherein the spikes are arranged in the first pattern; and
   (c) placing the probe head onto the conductive spikes, such that each stud is aligned with a respective spike.

* * * * *

UNITED STATES PATENT AND TRADEMARK OFFICE
CERTIFICATE OF CORRECTION

PATENT NO. : 6,215,317 B1
DATED : April 10, 2001
INVENTOR(S) : Shafiquil Siddiqui et al.

It is certified that error appears in the above-identified patent and that said Letters Patent is hereby corrected as shown below:

Title page, Item [54] and Column 1, lines 1-3,
Please correct the title to read as follows: -- METHOD AND APPARATUS FOR MEASURING IN-PLACE SOIL DENSITY AND MOISTURE CONTENT --.

Title page,
Item [75], Inventors, please change "Shafiqul" to -- Shafiquil --.
Please add Related U.S. Application Data as follows:
-- [62]   Division of application No. 09/098,908, June 17, 1998, Pat. No. 5,933,015, which is a division of application No. 08/705,606, August 30, 1996, Pat. No. 5,801,537.
   [60]   Provisional application No. 60/003,021, Aug. 30, 1995. --
Item [56], References Cited, FOREIGN PATENT DOCUMENTS, please add the following:       -- 1822967-A1   6/1993        U.S.S.R.
                1509-713-A    9/1989        U.S.S.R.
                1010-532-1    4/1983        U.S.S.R. --

Column 1,
Line 50, please change "robes" to -- probes --.

Column 2,
Line 40, please change "removable" to -- removably --.

Column 3,
Line 59, please change "step" to -- steps --.

Column 5,
Line 17, please change "ad" to -- and --.

Column 6,
Line 37, please change "of" to -- or --.

Column 7,
Line 25, please change "filed" to -- field -- and "dig" to -- dug --.

Column 8,
Line 6, please change "tow" to -- two --.

Column 9,
Line 56, please change "computer" to -- computed --.

Column 10,
Line 61, please change "access" to -- assess --.

UNITED STATES PATENT AND TRADEMARK OFFICE
CERTIFICATE OF CORRECTION

PATENT NO.     : 6,215,317 B1
DATED          : April 10, 2001
INVENTOR(S)    : Shafiquil Siddiqui et al.

It is certified that error appears in the above-identified patent and that said Letters Patent is hereby corrected as shown below:

Column 11,
Line 31, please change "filed" to -- field --.

Column 12,
Line 64, please change "9 inch" to -- 9 inches -- and "10 inch" to -- 10 inches --.

Column 13,
Line 66, please change "comparing" to -- Comparing --.

Column 14,
Line 11, please change "ration" to -- ratio --.

Column 15,
Line 25, please insert -- error -- after "any".
Line 29, please change "this" to -- thus --.
Line 63, please change "he" to -- the --.

Column 16,
Line 7, please insert -- of -- after "error".
Line 21, please change "know" to -- known --.
Line 36, please change "change" to -- changes --.

Signed and Sealed this

Seventh Day of October, 2003

JAMES E. ROGAN
*Director of the United States Patent and Trademark Office*